United States Patent
Kleeman

(10) Patent No.: US 7,446,225 B2
(45) Date of Patent: *Nov. 4, 2008

(54) PENTAFLUOROSULFANYLPHENYL-SUBSTITUTED BENZOYLGUANIDINES, METHOD FOR THE PRODUCTION THEREOF, THEIR USE AS A MEDICAMENT OR DIAGNOSTIC AGENT, AND A MEDICAMENT CONTAINING THESE COMPOUNDS

(75) Inventor: Heinz-Werner Kleeman, Bischofsheim (DE)

(73) Assignee: Sanofi-aventis Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/684,355

(22) Filed: Mar. 9, 2007

(65) Prior Publication Data

US 2007/0259963 A1 Nov. 8, 2007

Related U.S. Application Data

(63) Continuation of application No. PCT/EP2005/009272, filed on Aug. 27, 2005.

(30) Foreign Application Priority Data

Sep. 11, 2004 (DE) ........................ 10 2004 043 938

(51) Int. Cl.
*C07C 233/165* (2006.01)
*A61K 31/65* (2006.01)
(52) U.S. Cl. .................... 564/162; 564/134; 514/618
(58) Field of Classification Search ............... 564/134, 564/162; 514/618
See application file for complete search history.

(56) References Cited

U.S. PATENT DOCUMENTS

| 5,719,169 | A | 2/1998 | Kleemann et al. |
| 6,057,322 | A | 5/2000 | Kleemann et al. |
| 6,878,748 | B2 | 4/2005 | Kleemann |
| 2003/0216476 | A1* | 11/2003 | Kleemann ................ 514/618 |
| 2005/0043401 | A1 | 2/2005 | Kleemann |
| 2005/0124666 | A1 | 6/2005 | Kleemann |

OTHER PUBLICATIONS

Golub et al, Science, vol. 286, 1999, pp. 531-537.*

* cited by examiner

*Primary Examiner*—Shailendra Kumar
(74) *Attorney, Agent, or Firm*—Raymond S. Parker

(57) ABSTRACT

The invention relates to pentafluorosulfanylphenyl-substituted benzoylguanidines of the formula I:

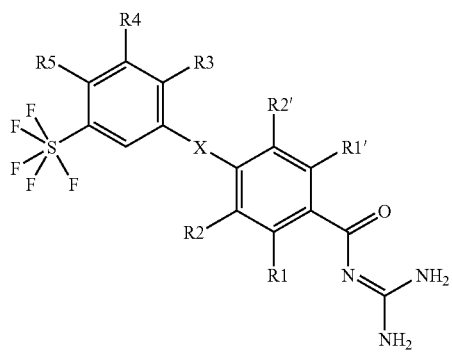

and a process for preparing a compound of the formula I and/or the pharmaceutically acceptable salts thereof.

9 Claims, No Drawings

PENTAFLUOROSULFANYLPHENYL-SUBSTITUTED BENZOYLGUANIDINES, METHOD FOR THE PRODUCTION THEREOF, THEIR USE AS A MEDICAMENT OR DIAGNOSTIC AGENT, AND A MEDICAMENT CONTAINING THESE COMPOUNDS

DETAILED DESCRIPTION OF THE INVENTION

The invention relates to pentafluorosulfanylphenyl-substituted benzoylguanidines of the formula I:

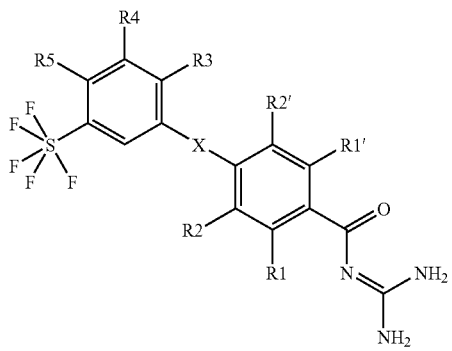

in which the meanings are

R1 and R1'
   independently of one another hydrogen, alkyl having 1, 2, 3 or 4 carbon atoms, alkoxy having 1, 2, 3 or 4 carbon atoms, F, Cl, Br, I, —CN, NR6R7, —O—$(CH_2)_b$—$(CF_2)_c$—$CF_3$ or —$(SO_d)_e$—$(CH_2)_f$—$(CF_2)_g$—$CF_3$;
   R6 and R7
      independently of one another hydrogen, alkyl having 1, 2, 3 or 4 carbon atoms or —$CH_2$—$CF_3$;
   d zero, 1 or 2;
   b, c, e, f and g
      independently of one another zero or 1;

R2 and R2'
   independently of one another hydrogen, F, Cl, Br, I, —CN, —$SO_2CH_3$, alkoxy having 1, 2, 3 or 4 carbon atoms, NR6R7, —O—$(CH_2)_b$—$(CF_2)_c$—$CF_3$, —$(SO_h)_k$—$(CH_2)_l$—$(CF_2)_m$—$CF_3$, alkyl having 1, 2, 3, 4, 5 or 6 carbon atoms, cycloalkyl having 3, 4, 5, 6, 7 or 8 carbon atoms, in which 1, 2, 3 or 4 hydrogen atoms may be replaced by fluorine atoms, —$(CH_2)_n$-phenyl which is unsubstituted or substituted by 1, 2 or 3 radicals selected from the group consisting of F, Cl, Br, I, —$O_o$—$(CH_2)_p$—$CF_3$, alkoxy having 1, 2, 3 or 4 carbon atoms, alkyl having 1, 2, 3 or 4 carbon atoms and —$SO_2CH_3$, or —$(CH_2)_q$-heteroaryl which is unsubstituted or substituted by 1, 2 or 3 radicals selected from the group consisting of F, Cl, Br, I, —$O_r$—$(CH_2)_s$—$CF_3$, alkoxy having 1, 2, 3 or 4 carbon atoms, alkyl having 1, 2, 3 or 4 carbon atoms and —$SO_2CH_3$;
   R6 and R7
      independently of one another hydrogen, alkyl having 1, 2, 3 or 4 carbon atoms or —$CH_2$—$CF_3$;
   b and c
      independently of one another zero or 1;
   h zero, 1 or 2;
   k zero or 1;
   l zero, 1, 2, 3, or 4;
   m and o
      independently of one another zero or 1;
   p zero, 1, 2 or 3;
   n zero, 1, 2, 3 or 4;
   r zero or 1;
   s zero, 1, 2 or 3;
   q zero, 1, 2, 3, or 4;

R3
   hydrogen, F, Cl, Br, I, —CN, —$SO_2CH_3$, alkyl having 1, 2, 3, 4, 5 or 6 carbon atoms, alkoxy having 1, 2, 3, or 4 carbon atoms or —$O_t$—$(CH_2)_u$—$CF_3$;
   t zero or 1;
   u zero, 1, 2 or 3;

R4 hydrogen, F, Cl, Br, I, —CN, —$SO_2CH_3$, NR6R7, —$(SO_v)_w$—$(CH_2)_x$—$(CF_2)_y$—$CF_3$, —O—$(CH_2)_{aa}$—$(CF_2)_{bb}$—$CF_3$, alkyl having 1, 2, 3, 4, 5 or 6 carbon atoms, alkoxy having 1, 2, 3 or 4 carbon atoms or cycloalkyl having 3, 4, 5, 6, 7 or 8 carbon atoms, in which 1, 2, 3 or 4 hydrogen atoms may be replaced by fluorine atoms;
   R6 and R7
      independently of one another hydrogen, alkyl having 1, 2, 3 or 4 carbon atoms or —$CH_2$—$CF_3$;
   v zero, 1 or 2;
   x zero, 1, 2, 3 or 4;
   w, y, aa and bb
      independently of one another zero or 1;

or
R4 —$(CH_2)_{cc}$-phenyl which is unsubstituted or substituted by 1, 2, or 3 radicals selected from the group consisting of F, Cl, Br, I, —$O_{dd}$—$(CH_2)_{ee}$—$CF_3$, alkoxy having 1, 2, 3 or 4 carbon atoms, alkyl having 1, 2, 3 or 4 carbon atoms and —$SO_2CH_3$;
   dd zero or 1;
   ee zero, 1, 2 or 3;
   cc zero, 1, 2, 3 or 4;

or
R4 —$(CH_2)_{ff}$-heteroaryl which is unsubstituted or substituted by 1, 2 or 3 radicals selected from the group consisting of F, Cl, Br, I, —$O_{gg}$—$(CH_2)_{hh}$—$CF_3$, alkoxy having 1, 2, 3 or 4 carbon atoms, alkyl having 1, 2, 3 or 4 carbon atoms and —$SO_2CH_3$;
   gg zero or 1;
   hh zero, 1, 2 or 3;
   ff zero, 1, 2, 3 or 4;

R5 F, Cl, Br, I, $CF_3$, —$SO_2CH_3$ or —$S(O)OCH_3$;
X a direct linkage, O, NR8, $S(O)_{kk}$;
   R8 hydrogen, alkyl having 1, 2, 3 or 4 carbon atoms, —$(CH_2)_{mm}$—$CF_3$ or —$SO_2CH_3$
   kk zero, 1 or 2;
   mm zero, 1, 2 or 3;

where —O—$(CH_2)_b$—$(CF_2)_c$—$CF_3$ in the definitions of R1 and R1' and R2 and R2' can be selected independently of one another, where NR6R7 in the definitions of R1 and R1', R2 and R2' and R4 can be selected independently of one another, and the pharmaceutically acceptable salts thereof.

Preference is given to compounds of the formula I in which the meanings are:
R1 and R1'
   independently of one another hydrogen, alkyl having 1, 2, 3 or 4 carbon atoms, methoxy, ethoxy, F, Cl, NR6R7, —O—$CH_2$—$CF_3$ or —$(SO_d)_e$—$(CH_2)_f$—$CF_3$;

R6 and R7
  independently of one another hydrogen, alkyl having 1, 2, 3 or 4 carbon atoms or —$CH_2$—$CF_3$;
d zero, 1 or 2;
e and f
  independently of one another zero or 1;
R2 and R2'
  independently of one another hydrogen, F, Cl, —$SO_2CH_3$, —$(SO_h)_k$—$(CH_2)_l$—$CF_3$, alkyl having 1, 2, 3 or 4 carbon atoms, cycloalkyl having 3, 4, 5, 6 or 7 carbon atoms, in which 1, 2, 3 or 4 hydrogen atoms may be replaced by fluorine atoms, phenyl which is unsubstituted or substituted by 1-2 radicals selected from the group consisting of F, Cl, —$O_o$—$(CH_2)_p$—$CF_3$, methoxy, ethoxy, alkyl having 1, 2, 3 or 4 carbon atoms and —$SO_2CH_3$, or heteroaryl which is unsubstituted or substituted by 1-2 radicals selected from the group consisting of F, Cl, —$O_r$—$(CH_2)_s$—$CF_3$, methoxy, ethoxy, alkyl having 1, 2, 3 or 4 carbon atoms and —$SO_2CH_3$;
h zero, 1 or 2;
k zero or 1;
l zero, 1, 2, 3, or 4;
o zero or 1;
p zero, 1, 2 or 3;
r zero or 1;
s zero, 1, 2 or 3;
R3 hydrogen, F, Cl, —$SO_2CH_3$, alkyl having 1, 2, 3 or 4 carbon atoms, methoxy, ethoxy or —$O_t$—$(CH_2)_u$—$CF_3$,
t zero or 1;
u zero, 1, 2 or 3;
R4 hydrogen, F, Cl, —$SO_2CH_3$, —$(SO_v)_w$—$(CH_2)_x$—$CF_3$, —O—$(CH_2)_{aa}$—$CF_3$, alkyl having 1, 2, 3 or 4 carbon atoms, methoxy, ethoxy or cycloalkyl having 3, 4, 5, 6 or 7 carbon atoms, in which 1, 2, 3 or 4 hydrogen atoms may be replaced by fluorine atoms;
v zero, 1 or 2;
w, x, and aa
  independently of one another zero or 1;

or
R4 phenyl which is unsubstituted or substituted by 1-2 radicals selected from the group consisting of F, Cl, —$O_{dd}$—$(CH_2)_{ee}$—$CF_3$, methoxy, ethoxy, alkyl having 1, 2, 3 or 4 carbon atoms and —$SO_2CH_3$;
dd and ee
  independently of one another zero or 1;

or
R4 heteroaryl which is unsubstituted or substituted by 1-2 radicals selected from the group consisting of F, Cl, —$O_{gg}$—$(CH_2)_{hh}$—$CF_3$, methoxy, ethoxy, alkyl having 1, 2, 3 or 4 carbon atoms and —$SO_2CH_3$;
gg and hh
  independently of one another zero or 1;
R5 F, Cl, $CF_3$, —$SO_2CH_3$ or —$S(O)OCH_3$;
X a direct linkage, O, NR8 or $S(O)_{kk}$;
  R8 hydrogen, alkyl having 1, 2, 3 or 4 carbon atoms, —$CH_2$—$CF_3$ or —$SO_2CH_3$;
  kk zero, 1 or 2;

and the pharmaceutically acceptable salts thereof.

Particular preference is given to compounds of the formula I in which the meanings are:
R1 and R1'
  independently of one another hydrogen, alkyl having 1, 2, 3 or 4 carbon atoms, methoxy, ethoxy, F, Cl, NR6R7, —O—$CH_2$—$CF_3$ or —$(SO_d)_e$—$(CH_2)_f$—$CF_3$;

R6 and R7
  independently of one another hydrogen, alkyl having 1, 2, 3 or 4 carbon atoms or —$CH_2$—$CF_3$;
d zero, 1 or 2;
e and f
  independently of one another zero or 1;
R2 and R2'
  independently of one another hydrogen, F, Cl, —$SO_2CH_3$, —$(SO_h)_k$—$(CH_2)_l$—$CF_3$, methyl, cycloalkyl having 3, 4, 5, 6 or 7 carbon atoms, in which 1, 2, 3 or 4 hydrogen atoms may be replaced by fluorine atoms, phenyl which is unsubstituted or substituted by a radical selected from the group consisting of F, Cl, —$O_o$—$(CH_2)_p$—$CF_3$, methoxy, ethoxy, alkyl having 1, 2, 3 or 4 carbon atoms and —$SO_2CH_3$, or heteroaryl which is unsubstituted or substituted by a radical selected from the group consisting of F, Cl, —$O_r$—$(CH_2)_s$—$CF_3$, methoxy, ethoxy, alkyl having 1, 2, 3 or 4 carbon atoms and —$SO_2CH_3$;
h zero, 1 or 2;
k, l, o, p, r and s
  independently of one another zero or 1;
R3 hydrogen, F, Cl, —$SO_2CH_3$, methyl, methoxy, ethoxy or —$O_t$—$(CH_2)_u$—$CF_3$;
t and u
  independently of one another zero or 1;
R4 hydrogen, F, Cl, —$SO_2CH_3$, —$(SO_v)_w$—$(CH_2)_x$—$CF_3$, —$O_z$—$(CH_2)_{aa}$—$CF_3$, methyl, methoxy, ethoxy or cycloalkyl having 3, 4, 5, 6 or 7 carbon atoms, in which 1, 2, 3 or 4 hydrogen atoms may be replaced by fluorine atoms;
v zero, 1 or 2;
w, x, z and aa
  independently of one another zero or 1;
R5 F, Cl or —$SO_2CH_3$;
X a direct linkage, O, NR8 or $S(O)_{kk}$;
  R8 hydrogen, methyl, ethyl, —$CH_2$—$CF_3$ or —$SO_2CH_3$;
  kk zero, 1 or 2;

and the pharmaceutically acceptable salts thereof.

Very particular preference is given to compounds of the formula I, in which the meanings are:
R1 and R1'
  independently of one another hydrogen, methyl, F, Cl, —$CF_3$ or —O—$CH_2$—$CF_3$;
R2 and R2'
  independently of one another hydrogen, F, Cl, —$SO_2CH_3$, —$SO_2$—$CF_3$, —$CF_3$ or methyl;
R3 hydrogen, F, Cl or methyl;
R4 hydrogen, F, Cl or methyl;
R5 —$SO_2CH_3$;
X O;

and the pharmaceutically acceptable salts thereof.

In one embodiment moreover preference is given to compounds of the formula I in which R1 and R1' are described independently of one another by hydrogen, methyl, F, Cl, —$CF_3$ or —O—$CH_2$—$CF_3$, and particular preference is given to compounds in which R1 and R1' are described independently of one another by hydrogen or methyl.

In a further embodiment, preference is given to compounds of the formula I in which R2 and R2' are described independently of one another by hydrogen, F, Cl, —$SO_2CH_3$, —$SO_2CF_3$, —$CF_3$ or methyl, and particular preference is given to compounds in which R2 and R2' are described independently of one another by hydrogen or —$SO_2CH_3$.

In a further embodiment, preference is given to compounds of the formula I in which R3 is described by hydrogen, F, Cl, —SO$_2$CH$_3$, methyl, —CF$_3$ or —O—CH$_2$—CF$_3$, and particular preference is given to compounds in which R3 is described by hydrogen.

In a further embodiment, preference is given to compounds of the formula I in which R4 is described by hydrogen, F, Cl, —SO$_2$CH$_3$, —O—CH$_2$—CF$_3$ or methyl, and particular preference is given to compounds in which R4 is described by hydrogen.

In a further embodiment, preference is given to compounds of the formula I in which R5 is described by F, Cl, CF$_3$, —SO$_2$CH$_3$ or —S(O)OCH$_3$, in particular by —SO$_2$CH$_3$.

In a further embodiment, preference is given to compounds of the formula I in which X is a direct linkage or is described by O, NR8 or S(O)$_{kk}$, where R8 is hydrogen, methyl, ethyl, —CH$_2$—CF$_3$ or —SO$_2$CH$_3$, preferably hydrogen or methyl, and where kk is zero, 1 or 2, preferably zero or 2; and particular preference is given to compounds of the formula I in which X is described by O.

Radicals which occur more than once may be identical or different and independently of one another have the stated meanings.

Especially preferred are N-[5-methanesulfonyl-4-(4-methanesulfonyl-3-pentafluorosulfanylphenoxy)-2-methylbenzoyl]guanidine and its pharmaceutically acceptable salts.

If the substituents R1, R1', R2, R2', R3, R4 or R5 contain one or more centers of asymmetry, these may independently of one another have both the S and the R configuration. The compounds may be in the form of optical isomers, of diastereomers, of racemates or of mixtures thereof in any ratio.

The present invention encompasses all tautomeric forms of the compounds of the formula I.

Alkyl radicals may be straight-chain or branched. This also applies if they carry substituents or occur as substituents of other radicals, for example in fluoroalkyl radicals, alkoxy radicals, fluoroalkoxy radicals, alkylamino radicals, dialkylamino radicals and alkylsulfonyl radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), pentyl and hexyl. Preferred alkyl radicals are methyl, ethyl, n-propyl and isopropyl, particularly preferably methyl and ethyl. One or more, for example 1, 2, 3, 4 or 5, hydrogen atoms in alkyl radicals may be replaced by fluorine atoms. Examples of such fluoroalkyl radicals are trifluoromethyl, 2,2,2-trifluoroethyl and pentafluoroethyl. Substituted alkyl radicals may be substituted in any positions.

Examples of cycloalkyl radicals are cyclopropyl, cyclobutyl, cyclopentyl, cyclohexyl, cycloheptyl or cyclooctyl. One or more, for example 1, 2, 3 or 4, hydrogen atoms in cycloalkyl radicals may be replaced by fluorine atoms. Substituted cycloalkyl radicals may be substituted in any positions.

Phenyl radicals may be unsubstituted or be substituted one or more times, for example once, twice or three times, by identical or different radicals. This likewise applies to phenyl radicals in groups such as, for example, phenylalkyl or phenyloxy. The substituent in monosubstituted phenyl radicals may be in position 2, position 3 or position 4. Disubstituted phenyl may be substituted in the 2,3 position, 2,4 position, 2,5 position, 2,6 position, 3,4 position or 3,5 position. The substituents in trisubstituted phenyl radicals may be in the 2,3,4 position, 2,3,5 position, 2,4,5 position, 2,4,6 position, 2,3,6 position or 3,4,5 position.

Heteroaryl radicals are aromatic ring compounds in which one or more ring atoms are oxygen atoms, sulfur atoms or nitrogen atoms, e.g. 1, 2 or 3 nitrogen atoms, 1 or 2 oxygen atoms, 1 or 2 sulfur atoms or a combination of various heteroatoms. The heteroaryl radicals may be attached by all positions, for example by the 1 position, 2 position, 3 position, 4 position, 5 position, 6 position, 7 position or 8 position.

Heteroaryl radicals may be unsubstituted or be substituted one or more times, for example once, twice or three times, by identical or different radicals. This applies likewise to heteroaryl radicals such as, for example, in the radical heteroarylalkyl. Examples of heteroaryl are furyl, thienyl, pyrrolyl, imidazolyl, pyrazolyl, triazolyl, tetrazolyl, oxazolyl, isoxazolyl, oxadiazolyl, thiadiazolyl, thiazolyl, isothiazolyl, pyridyl, pyrazinyl, pyrimidinyl, pyridazinyl, indolyl, benzimidazolyl, indazolyl, quinolyl, isoquinolyl, phthalazinyl, quinoxalinyl, quinazolinyl and cinnolinyl.

Heteroaryl radicals are, in particular, 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4-oxadiazol-3- or -5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or -5-yl, 2-, 3- or 4-pyridyl, 2-, 4-, 5- or 6-pyrimidinyl, 3- or 4-pyridazinyl, 2- or 3-pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl. Also encompassed are the corresponding N-oxides of these compounds, i.e. for example 1-oxy-2-, 3- or 4-pyridyl. Particularly preferred heteroaryl radicals are 2- or 3-thienyl, 2- or 3-furyl, 1-, 2- or 3-pyrrolyl, 1-, 2-, 4- or 5-imidazolyl, 2-, 3-, 4-, 5-, 6-, 7- or 8-quinolyl, 1-, 3-, 4- or 5-pyrazolyl, 2-, 3- or 4-pyridyl, 2- or 3-pyrazinyl, 2-, 4-, 5- or 6-pyrimidinyl and 3- or 4-pyridazinyl.

The present invention also relates to the processes described below for preparing the compounds of the formula I.

The present invention relates to a process for preparing a compound of the formula I and/or the pharmaceutically acceptable salts thereof in which X is oxygen (scheme 1), which comprises a) reacting a phenol of the formula III with an aromatic compound of the formula IV to give a compound of the formula V, b) introducing R5 by electrophilic aromatic substitution and converting to a compound of the formula VI and c) reacting a compound of the formula VI with guanidine to give the acylguanidine of the formula Ia,

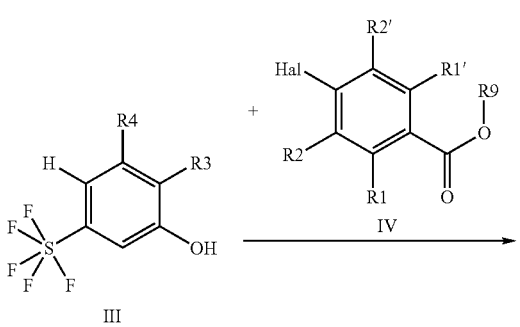

Scheme 1

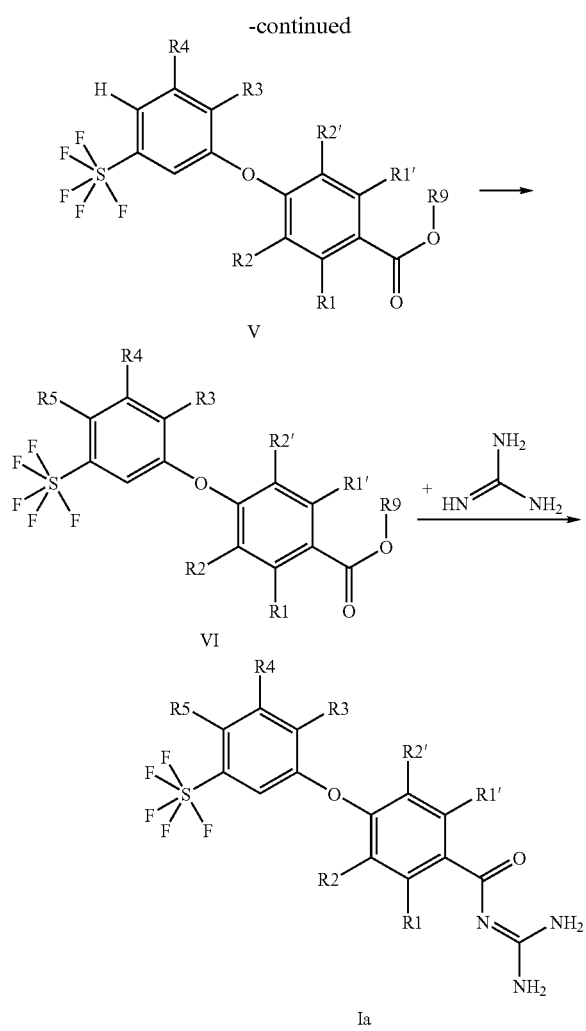

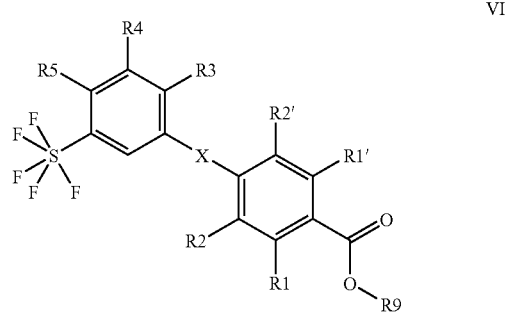

in which R1, R1', R2, R2', R3, R4 and R5 have the meaning indicated above, and in which the meanings are Hal F, Cl, Br or I, R9 hydrogen or alkyl having 1, 2, 3 or 4 carbon atoms.

The phenols of the formulae III are deprotonated in a suitable solvent, preferably in a dipolar aprotic solvent such as, for example, acetonitrile, DMF, NMP or DMSO, with the aid of an inorganic base such as, for example, $K_2CO_3$ or $Cs_2CO_3$, or with the aid of an organic base such as, for example, triethylamine or TBTMG, at a temperature between 0° C. and the boiling point of the solvent used, and then reacted with the electrophilic aromatic compound of the formula IV in a nucleophilic aromatic substitution at a temperature between 0° C. and the boiling point of the solvent used, preferably between RT and 150° C., to give compounds of the formula V.

Conversion of the compounds of the formula V into compounds of the formula VI takes place by electrophilic aromatic substitution, preferably by nitration, as described for example in Houben-Weyl, Methoden der organischen Chemie 4th edition, Organo-Stickstoff-Verbindungen IV, Part 1, Georg Thieme Verlag Stuttgart 1992, pp. 262-341 and the literature cited therein. Nitration is preferably carried out with 90% $HNO_3$ at a temperature between −80° C. and RT, particularly preferably between −60° C. and 0° C. It is possible to prepare from the compounds of the formula VI with R5=$NO_2$ the corresponding anilines (R5=$NH_2$) as described in R. C. Larock, Comprehensive Organic Transformations: A Guide to Functional Group Preparations, VCH Publishers, New York, Weinheim, 1999, 821-828 and the literature cited therein. The compounds of the formula VI with further meanings of R5 are synthesized from these anilines via the diazonium salts by a method known to the skilled worker, as described for example in Houben-Weyl, Methoden der organischen Chemie 4th edition, Organo-Stickstoff-Verbindungen I, Part 2, Georg Thieme Verlag Stuttgart 1990, pp. 1060-1136 and the literature cited therein.

The reaction of the compounds of the formula VI to give the acylguanidines of the formula Ia takes place either with free guanidine base or, preferably, with guanidinium chloride which is initially stirred together with KOtBu in an inert solvent, preferably DMF or NMP, and then stirred together with the ester at a temperature between 0° C. and the boiling point of the solvent, preferably between RT and 100° C.

The esters of the formula V in which R9 is alkyl can also be initially hydrolyzed to the carboxylic acids and then reacted, preferably in the presence of an activating agent, with guanidine to give acylguanidines of the formula Ia.

The starting compounds of the formulae III and IV can be obtained commercially or can be prepared in analogy to processes known to the skilled worker and described in the literature.

It is also possible for functional groups in the starting compounds to be present in protected form or in the form of precursors and then to be converted into the desired groups in the compounds of the formula I prepared by the process described above. Appropriate protective group techniques are known to the skilled worker.

The working up and, if desired, the purification of the products and/or intermediates takes place by conventional methods such as extraction, chromatography or crystallization and conventional dryings.

The invention also includes precursors of the formula VI and the salts thereof where R1, R1', R2, R2', R3, R4, R5 and X have the above-mentioned meanings, and R9 is hydrogen or alkyl having 1, 2, 3 or 4 carbon atoms, and the use thereof as synthetic intermediates, for example for preparing active pharmaceutical ingredients such as, for example, compounds of the formula I and/or the pharmaceutically acceptable salts thereof by reaction with guanidine.

Pentafluorosulfanylphenyl-substituted benzoylguanidines of the formula I are generally weak bases and are able to bind acid to form salts. Suitable acid addition salts are in particular salts of all pharmacologically acceptable acids, for example halides, in particular hydrochlorides, lactates, sulfates, citrates, tartrates, acetates, phosphates, methylsulfonates, p-toluenesulfonates.

The compounds of the formula I are substituted acylguanidines and inhibit the cellular sodium-proton antiporter (Na$^+$/H$^+$ exchanger, NHE), especially the NHE-1 subtype.

Compared with known NHE inhibitors, the compounds of the invention are distinguished by an extremely high activity in the inhibition of Na$^+$/H$^+$ exchange, and by improved ADMET properties, for example by longer S9 stabilities (liver stabilities, stability to enzymatic attack) and greater selectivity in relation to the hERG potassium channel. They moreover show good absorption characteristics and a high bioavailability.

Because of the NHE-inhibitory properties, the compounds of the formula I and/or the pharmaceutically acceptable salts thereof are suitable for the prevention and treatment of diseases caused by activation or activated NHE, and of diseases caused secondarily by the NHE-related damage.

Since NHE inhibitors predominantly act via their effect on cellular pH regulation, they can generally be combined beneficially with other compounds which regulate the intracellular pH, with suitable combination partners being inhibitors of the carbonic anhydratase enzyme group, inhibitors of systems transporting bicarbonate ions, such as of the sodium bicarbonate cotransporter (NBC) or of the sodium-dependent chloride-bicarbonate exchanger (NCBE), and NHE inhibitors with inhibitory effect on other NHE subtypes, because it is possible through them to enhance or modulate the pharmacologically relevant pH-regulating effects of the NHE inhibitors described herein.

The use of the compounds of the invention relates to the prevention and treatment of acute and chronic diseases in veterinary and human medicine.

Thus, the NHE inhibitors of the invention are suitable for the treatment of diseases caused by ischemia and by reperfusion.

The compounds described herein are suitable because of their pharmacological properties as antiarrhythmic medicaments.

Owing to their cardioprotective component, the NHE inhibitors are outstandingly suitable for infarction prophylaxis and infarction treatment and for the treatment of angina pectoris, in which cases they also preventively inhibit or greatly reduce the pathophysiological processes associated with the development of ischemia-induced damage, in particular in the triggering of ischemia-induced cardiac arrhythmias. Because of their protective effects against pathological hypoxic and ischemic situations, the compounds of the formula I and/or the pharmaceutically acceptable salts thereof used according to the invention can, because of inhibition of the cellular Na$^+$/H$^+$ exchange mechanism, be used as medicaments for the treatment of all acute or chronic ischemia-induced damage or diseases induced primarily or secondarily thereby.

This also relates to their use as medicaments for surgical interventions. Thus, the compounds can be used during organ transplantations, it being possible to use the compounds both to protect the organs in the donor before and during the removal, to protect removed organs for example during treatment with or storage thereof in physiological bath liquids, and during transfer into the recipient organism.

The compounds of the invention are likewise valuable medicaments with a protective effect when performing angioplastic surgical interventions, for example on the heart as well as on peripheral organs and vessels.

The compounds of the invention can further be used when performing bypass operations, for example during bypass operations on coronary vessels and in Coronary Artery Bypass Graft (CABG).

In accordance with their effect on ischemia-induced damage, the compounds of the invention of the formula I can also be employed for resuscitation following a cardiac arrest.

The compounds of the invention are of interest for medicaments for life-threatening arrhythmias. Ventricular fibrillation is terminated and the physiological sinus rhythm of the heart is restored.

Since NHE1 inhibitors of human tissue and organs, especially the heart, protect effectively not only against damage caused by ischemia and reperfusion but also against the cytotoxic effect of medicaments like those used in particular in cancer therapy and the therapy of autoimmune diseases, combined administration with compounds of the formula I and/or the pharmaceutically acceptable salts thereof is suitable for inhibiting the cytotoxic, especially cardiotoxic, side effects of said compounds. The reduction in the cytotoxic effects, especially the cardiotoxicity, resulting from comedication with NHE1 inhibitors makes it additionally possible to increase the dose of the cytotoxic therapeutic agents and/or to prolong the medication with such medicaments. The therapeutic benefits of such a cytotoxic therapy can be considerably increased by combination with NHE inhibitors.

In addition, the NHE1 inhibitors of the invention of the formula I and/or the pharmaceutically acceptable salts thereof can be used when there is heart-damaging overproduction of thyroid hormones, thyrotoxicosis, or on external supply of thyroid hormones. The compounds of the formula I and/or the pharmaceutically acceptable salts thereof are thus suitable for improving therapy with cardiotoxic medicaments.

In accordance with their protective effect against ischemia-induced damage, the compounds of the invention are also suitable as medicaments for the treatment of ischemias of the nervous system, especially of the central nervous system, these being suitable for example for the treatment of stroke or of cerebral edema.

The compounds of the formula I and/or the pharmaceutically acceptable salts thereof are also suitable for the therapy and prophylaxis of diseases and disorders induced by overexcitability of the central nervous system, in particular for the treatment of epileptic disorders, centrally induced clonic and tonic spasms, states of psychological depression, anxiety disorders and psychoses. In these cases it is possible to use the NHE inhibitors described herein alone or in combination with other substances with antiepileptic activity or antipsychotic active ingredients, or carbonic anhydrase inhibitors, for example with acetazolamide, and with other inhibitors of NHE or of the sodium-dependent chloride-bicarbonate exchanger (NCBE).

The compounds used according to the invention of the formula I and/or the pharmaceutically acceptable salts thereof are additionally likewise suitable for the treatment of types of shock such as, for example, of allergic, cardiogenic, hypovolemic and bacterial shock.

The compounds of the formula I and/or the pharmaceutically acceptable salts thereof can likewise be used for the prevention and treatment of thrombotic disorders because they, as NHE inhibitors, are able to inhibit platelet aggregation themselves. They are additionally able to inhibit or prevent the excessive release, occurring after ischemia and reperfusion, of mediators of inflammation and coagulation, especially of von Willebrand factor and of thrombogenic selectin proteins. It is thus possible to reduce and eliminate the pathogenic effect of significant thrombogenic factors. The NHE inhibitors of the present invention can therefore be combined with other anticoagulant and/or thrombolytic active ingredients such as, for example, recombinant or natural tissue plasminogen activator, streptokinase, urokinase, acetylsalicylic acid, thrombin antagonists, factor Xa antagonists, medicinal substances with fibrinolytic activity, thromboxane receptor antagonists, phosphodiesterase inhibitors, factor VIIa antagonists, clopidogrel, ticlopidine etc. Combined use of the present NHE inhibitors with NCBE inhibitors and/or with inhibitors of carbonic anhydrase such as, for example, with acetazolamide, is particularly beneficial.

NHE1 inhibitors are additionally distinguished by a strong inhibitory effect on the proliferation of cells, for example fibroblast proliferation and the proliferation of smooth vascular muscle cells. The compounds of the formula I and/or the pharmaceutically acceptable salts thereof are therefore suitable as valuable therapeutic agents for diseases in which cellular proliferation represents a primary or secondary cause, and can therefore be used as antiatherosclerotics, agents for chronic renal failure, cancers.

It was possible to show that cell migration is inhibited by NHE inhibitors. The compounds of the formula I and/or the pharmaceutically acceptable salts thereof are therefore suitable as valuable therapeutic agents for diseases in which cell migration represents a primary or secondary cause, such as, for example, cancers with a pronounced tendency to metastasis.

NHE1 inhibitors are further distinguished by a retardation or prevention of fibrotic disorders. The compounds of the formula I and/or the pharmaceutically acceptable salts thereof are thus suitable as agents for the treatment of cardiac fibroses, and of pulmonary fibrosis, hepatic fibrosis, renal fibrosis and other fibrotic disorders. They can thus be used for the treatment of organ hypertrophies and hyperplasias, for example of the heart and the prostate. They are therefore suitable for the prevention and treatment of heart failure (congestive heart failure=CHF) and for the treatment and prevention of prostate hyperplasia or prostate hypertrophy.

Since there is significant elevation in NHE in essential hypertensives, the compounds of the formula I and/or the pharmaceutically acceptable salts thereof are suitable for the prevention and treatment of high blood pressure and for the treatment of cardiovascular disorders. In these cases they can be used alone or with a suitable combination and formulation partner for the treatment of high blood pressure and of cardiovascular disorders. Thus, for example, one or more diuretics with a thiazide-like action, loop diuretics, aldosterone and pseudoaldosterone antagonists, such as hydrochlorothiazide, indapamide, polythiazide, furosemide, piretamide, torasemide, bumetamide, amiloride, triamterene, spironolactone or eplerone, can be combined. The NHE inhibitors of the present invention can further be used in combination with calcium channel blockers such as verapamil, diltiazem, amlodipine or nifedipine, and with ACE inhibitors such as, for example, ramipril, enalapril, lisinopril, fosinopril or captopril. Further beneficial combination partners are also beta-blockers such as metoprolol, albuterol etc., antagonists of the angiotensin receptor and its receptor subtypes such as losartan, irbesartan, valsartan, omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of Kv1.5 etc.

It has emerged that NHE1 inhibitors have a significant antiinflammatory effect and can thus be used as antiinflammatory drugs. Inhibition of the release of mediators of inflammation is noteworthy in this connection. The compounds can thus be used alone or in combination with an antiinflammatory drug for the prevention or treatment of chronic and acute inflammatory disorders. Combination partners advantageously used are steroidal and non-steroidal antiinflammatory drugs.

The compounds of the invention can also be used to treat diseases caused by protozoa, such as malaria or coccidiosis in poultry.

It has additionally been found that NHE1 inhibitors show a beneficial effect on serum lipoproteins. It is generally acknowledged that blood fat levels which are too high, called hyperlipoproteinemias, represent an essential risk factor for the development of arteriosclerotic vascular lesions, especially coronary heart disease. The reduction of elevated serum lipoproteins therefore has exceptional importance for the prophylaxis and regression of atherosclerotic lesions. Besides the reduction in total serum cholesterol, it is particularly important to reduce the proportion of specific atherogenic lipid fractions of this total cholesterol, in particular of the low density lipoproteins (LDL) and of the very low density lipoproteins (VLDL), because these lipid fractions represent an atherogenic risk factor. By contrast, a protective function against coronary heart disease is ascribed to the high density lipoproteins. Accordingly, hypolipidemics should be able to reduce not only total cholesterol but, in particular, the VLDL and LDL serum cholesterol fractions. It has now been found that NHE1 inhibitors show valuable therapeutically utilizable properties in relation to influencing the serum lipid levels.

Thus, they significantly reduce the elevated serum concentrations of LDL and VLDL as observed, for example, due to increased dietary intake of a cholesterol- and lipid-rich diet or in cases of pathological metabolic alterations, for example genetically related hyperlipidemias. They can therefore be used for the prophylaxis and regression of atherosclerotic lesions by eliminating a causal risk factor. Included herein are not only the primary hyperlipidemias but also certain secondary hyperlipidemias occurring, for example, in association with diabetes. In addition, the NHE1 inhibitors lead to a marked reduction in the infarctions induced by metabolic abnormalities and, in particular, to a significant reduction in the induced infarct size and the severity thereof.

The compounds of the formula I and/or the pharmaceutically acceptable salts thereof are therefore advantageously used for producing a medicament for the treatment of hypercholesterolemia; for producing a medicament for the prevention of atherogenesis; for producing a medicament for the prevention and treatment of atherosclerosis, for producing a medicament for the prevention and treatment of diseases induced by elevated cholesterol levels, for producing a medicament for the prevention and treatment of diseases induced by endothelial dysfunction, for producing a medicament for the prevention and treatment of atherosclerosis-induced hypertension, for producing a medicament for the prevention and treatment of atherosclerosis-induced thromboses, for producing a medicament for the prevention and treatment of hypercholesterolemia-induced and endothelial dysfunction-induced ischemic damage and post-ischemic reperfusion damage, for producing a medicament for the prevention and treatment of hypercholesterolemia-induced and endothelial dysfunction-induced cardiac hypertrophies and cardiomyopathies and of congestive heart failure (CHF), for producing a medicament for the prevention and treatment of hypercholesterolemia-induced and endothelial dysfunction-induced coronary vasospasms and myocardial infarctions, for producing a medicament for the treatment of said disorders in combinations with hypotensive substances, preferably with angiotensin converting enzyme (ACE) inhibitors and angiotensin receptor antagonists. A combination of an NHE inhibitor of the formula I and/or the pharmaceutically acceptable salts thereof with an active ingredient lowering the blood fat levels, preferably with an HMG-CoA reductase inhibitor (for example lovastatin or pravastatin), the latter bringing about a hypolipidemic effect and thus increasing the hypolipidemic properties of the NHE inhibitor of the formula I and/or the pharmaceutically acceptable salts thereof, proves to be a favorable combination with enhanced effect and reduced use of active ingredients.

Thus, compounds of the formula I and/or the pharmaceutically acceptable salts thereof lead to effective protection against endothelial damage of various origins. This protection of the vessels against the syndrome of endothelial dysfunction means that the compounds of the formula I and/or the pharmaceutically acceptable salts thereof are valuable medicaments for the prevention and treatment of coronary vasospasms, peripheral vascular diseases, in particular intermittent claudication, atherogenesis and atherosclerosis, left ventricular hypertrophy and dilated cardiomyopathy and thrombotic disorders.

It has additionally been found that NHE1 inhibitors are suitable in the treatment of non-insulin-dependent diabetes (NIDDM), with the insulin resistance being restrained. It may in this connection be beneficial, to enhance the antidiabetic activity and quality of the effect of the compounds of the invention, to combine them with a biguamide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

Besides the acute antidiabetic effects, the compounds of the formula I and/or the pharmaceutically acceptable salts thereof counteract the development of late complications of diabetes and can therefore be used as medicaments for the prevention and treatment of late damage from diabetes, such as diabetic nephropathy, diabetic neuropathy, diabetic retinopathy, diabetic cardiomyopathy and other disorders occurring as a consequence of diabetes. They can in this connection be advantageously combined with the antidiabetic medicaments just described under NIDDM treatment. The combination with a beneficial dosage form of insulin should be particularly important in this connection.

NHE1 inhibitors show, besides the protective effects against acute ischemic events and the subsequent equally acutely stressing reperfusion events, also direct therapeutically utilizable effects against diseases and disorders of the entire mammalian organism which are associated with the manifestations of the chronically progressive aging process and which occur independently of acute ischemic states and under normal, non-ischemic conditions. These pathological, age-related manifestations induced over the long aging period, such as illness, invalidity and death, which can now be made amenable to treatment with NHE inhibitors, are diseases and disorders which are essentially caused by age-related changes in vital organs and the function thereof and become increasingly important in the aging organism.

Disorders connected with an age-related functional impairment or with age-related manifestations of wear of organs are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. One important function and a measure of the maintenance of the reactivity of vessels is the blockade or retardation of the age-related progression in endothelial dysfunction, which can be eliminated highly significantly by NHE inhibitors. The compounds of the formula I and/or the pharmaceutically acceptable salts thereof are thus outstandingly suitable for the treatment and prevention of the age-related progression in endothelial dysfunction, especially of intermittent claudication.

An example of another variable characterizing the aging process is the decline in the contractability of the heart and the decline in the adaptation of the heart to a required pumping output of the heart. This diminished efficiency of the heart as a consequence of the aging process is in most cases connected with a dysfunction of the heart which is caused inter alia by deposition of connective tissue in the myocardial tissue. This deposition of connective tissue is characterized by an increase in the weight of the heart, by an enlargement of the heart and by restrictive cardiac function. It was surprising that it was possible almost completely to inhibit such aging of the heart organ. The compounds of the formula I and/or the pharmaceutically acceptable salts thereof are thus outstandingly suitable for the treatment and prevention of heart failure, of congestive heart failure (CHF). Not only is it possible to cure a cancer which has already occurred through inhibition of proliferation, but there is also reduction and highly significant retardation of the age-related incidence of cancer through NHE inhibitors. A particularly noteworthy finding is that the disorders, occurring as a result of aging, of all organs and not only certain types of cancer are suppressed or occur with a highly significant delay. The compounds of the formula I and/or the pharmaceutically acceptable salts thereof are thus outstandingly suitable for the treatment and, in particular, the prevention of age-related types of cancer.

With NHE inhibitors there is now found to be not only a delay, shifted highly significantly in time and beyond the normal statistical extent, in the occurrence of age-related disorders of all the organs investigated, including the heart, vessels, liver etc., but also a highly significant delay in cancer of the elderly. On the contrary, there is also surprisingly a prolongation of life to an extent which has to date been achievable by no other group of medicaments or by any natural products. This unique effect of NHE inhibitors also makes it possible, besides the use of the active ingredients alone on humans and animals, to combine these NHE inhibitors with other active principles, measures, substances and natural products which are used in gerontology and which are based on a different mechanism of action. Such classes of active ingredients used in gerontological therapy are: in particular vitamins and substances with antioxidant activity. Since there is a correlation between caloric load or food intake and the aging process, the combination with dietary measures can take place for example with appetite suppressants. It is likewise possible to consider a combination with hypotensive medicaments such as with ACE inhibitors, angiotensin receptor antagonists, diuretics, $Ca^{2+}$ channel blockers etc. or with metabolism-normalizing medicaments such as cholesterol-lowering agents.

The compounds of the formula I and/or the pharmaceutically acceptable salts thereof are thus outstandingly suitable for the prevention of age-related tissue changes and for prolonging life while retaining a high quality of life.

The compounds of the invention are effective inhibitors of the cellular sodium-proton antiporter (Na/H exchanger)

which in a large number of disorders (essential hypertension, atherosclerosis, diabetes etc.) is also increased in cells which are readily amenable to measurements, such as, for example, in erythrocytes, platelets or leucocytes. The compounds used according to the invention are therefore suitable as outstanding and simple scientific tools, for example in their use as diagnostic agents for determining and distinguishing different types of hypertension, but also of atherosclerosis, diabetes and the late complications of diabetes, proliferative disorders etc.

Also claimed is a medicine for human, veterinary or phytoprotective use, comprising an effective amount of a compound of the formula I and/or the pharmaceutically acceptable salts thereof, together with pharmaceutically acceptable carriers and additives, alone or in combination with other pharmacological active ingredients or medicaments.

Medicaments which comprise a compound of the formula I and/or the pharmaceutically acceptable salts thereof can in this connection be administered, for example, orally, parenterally, intravenously, rectally, percutaneously or by inhalation, the preferred administration being dependent on the particular characteristics of the disorder. The compounds of the formula I may moreover be used alone or together with pharmaceutical excipients, both in veterinary medicine and in human medicine. The medicaments generally comprise active ingredients of the formula I and/or the pharmaceutically acceptable salts thereof in an amount of from 0.01 mg to 1 g per dose unit.

The excipients suitable for the desired pharmaceutical formulation are familiar to the skilled worker on the basis of his expert knowledge. Besides solvents, gel formers, suppository bases, tablet excipients, and other active ingredient carriers, it is possible to use, for example, antioxidants, dispersants, emulsifiers, antifoams, flavorings, preservatives, solubilizers or colors.

For a form for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

For subcutaneous, intramuscular or intravenous administration, the active compounds used are converted, if desired with the substances customary for this purpose, such as solubilizers, emulsifiers or other excipients, into a solution, suspension or emulsion.

Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I and/or the pharmaceutically acceptable salts thereof in a pharmaceutically acceptable solvent such as, in particular, ethanol or water, or a mixture of such solvents. The formulation may, if required, also contain other pharmaceutical excipients such as surfactants, emulsifiers and stabilizers, and a propellant gas. Such a preparation normally contains the active ingredient in a concentration of about 0.1 to 10, in particular of about 0.3 to 3% by weight.

The dosage of the active ingredient of the formula I to be administered, and the frequency of administration, depend on the potency and duration of action of the compounds used; additionally also on the nature and severity of the disorder to be treated and on the sex, age, weight and individual responsiveness of the mammal to be treated.

On average, the daily dose of a compound of the formula I and/or the pharmaceutically acceptable salts thereof for a patient weighing about 75 kg is at least 0.001 mg/kg, e.g. 0.01 mg/kg, to a maximum of 10 mg/kg, e.g. 1 mg/kg, of body weight. For acute episodes of the disorder, for example immediately after suffering a myocardial infarction, higher dosages may also be necessary, e.g. up to 4 single doses a day. Up to 700 mg a day may be necessary, in particular on i.v. administration, for example for a patient with infarction in the intensive care unit, and the compounds of the invention can be administered by infusion.

List of abbreviations:

| | |
|---|---|
| ADMET | absorption - distribution - metabolism - excretion - toxicology |
| DIP | diisopropyl ether |
| DMF | N,N-dimethylformamide |
| DMSO | dimethyl sulfoxide |
| EA | ethyl acetate |
| HEP | n-heptane |
| hERG | human ether-a-go-go-related gene |
| HOAc | acetic acid |
| KOtBu | potassium 2-methylpropan-2-olate |
| MeOH | methanol |
| mp | melting point |
| MTB | tert-butyl methyl ether |
| NMP | 1-methylpyrrolidin-2-one |
| RT | room temperature |
| TBTMG | N"-tert-butyl-N,N,N',N'-tetramethylguanidine |
| THF | tetrahydrofuran |

EXAMPLE 1

N-[5-methanesulfonyl-4-(4-methanesulfonyl-3-pentafluorosulfanyl-phenoxy)-2-methylbenzoyl]guanidine

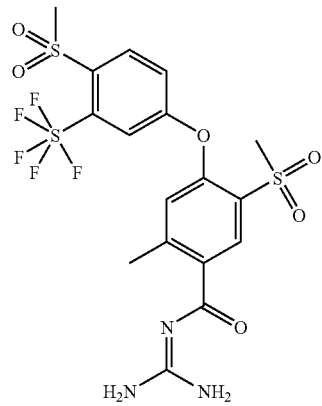

a) 3-Pentafluorosulfanylphenol

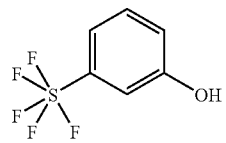

5.0 g of 3-pentafluorosulfanylaniline were suspended in 50 ml of a 35% aqueous H₂SO₄ solution. Then, at 0° C., a solution of 1.57 g of NaNO₂ in 5 ml of water was added dropwise over the course of 10 minutes. The mixture was stirred at 0° C. for 40 minutes. Then a solution, cooled to 0° C., of 8.56 g of Cu(NO₃)₂ in 50 ml of water was added to this suspension. Immediately thereafter, 3.26 g of Cu₂O was also added, whereupon marked evolution of gas was observable. 3 extractions each with 100 ml of CH₂Cl₂ were carried out, the org. phase washed with 100 ml of a saturated aqueous NaCl solution and dried over MgSO₄, and the solvent was removed in vacuo. Chromatography with DIP on a short silica gel column afforded 3.5 g of the phenol as colorless oil.

| R_f (EA/HEP 1:10) = 0.15 | MS (EI): 220 |
|---|---| b) Methyl 5-methanesulfonyl-2-methyl-4-(3-pentafluorosulfanylphenoxy)benzoate

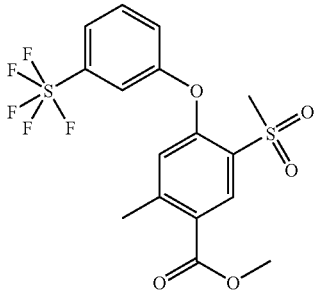

600 mg of methyl 4-fluoro-5-methanesulfonyl-2-methyl-benzoate, 700 mg of 3-pentafluorosulfanylphenol and 1.6 g of Cs₂CO₃ were stirred in 4 ml of anhydrous DMF at 100° C. for 3 h. The mixture was then cooled to RT, diluted with 100 ml of EA and washed 3 times with 20 ml of water each time. The residue after drying over MgSO₄ and removal of the solvent in vacuo was chromatographed on silica gel with DIP. 300 mg of a colorless oil were obtained.

| R_f (DIP) = 0.27 | MS (ES⁺): 446 |
|---|---| c) Methyl 5-methanesulfonyl-4-(4-nitro-3-pentafluorosulfanylphenoxy)-2-methyl-benzoate

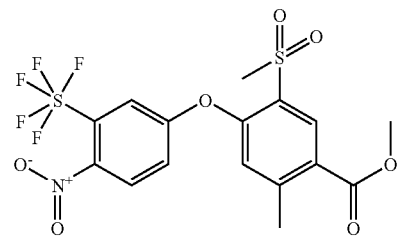

3.50 g of methyl 5-methanesulfonyl-2-methyl-4-(3-pentafluorosulfanylphenoxy)-benzoate were dissolved in 100 ml of 90% HNO₃ at −40° C. The reaction mixture was stirred at this temperature for 10 minutes and then poured into 800 g of ice. This mixture was stirred for 10 minutes and then the product was filtered off with suction. 3.89 g of a pale yellow solid were obtained, mp 145-148° C. (with decomposition). R_f(DIP)=0.09 d) Methyl 4-(4-amino-3-pentafluorosulfanylphenoxy)-5-methanesulfonyl-2-methyl-benzoate

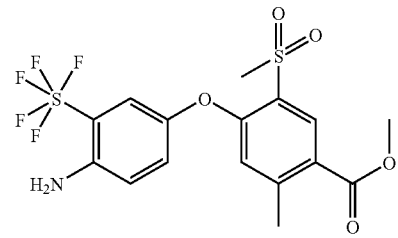

3.80 g of methyl 5-methanesulfonyl-4-(4-nitro-3-pentafluorosulfanylphenoxy)-2-methyl-benzoate were dissolved in 30 ml of HOAc and 30 ml of MeOH, 200 mg of Pd/C (10%) were added, and hydrogenation was carried out under a pressure of 6 bar of hydrogen for 24 h. Since reaction was still incomplete, a further 300 mg of Pd/C (10%), 30 ml of HOAc and 30 ml of MeOH was added, and hydrogenation was continued under a pressure of 6 bar of hydrogen for 24 h. The catalyst was then filtered off and the solvents were removed in vacuo. 3.4 g of a pale gray solid were obtained, mp 175° C. (with decomposition).
R_f(MTB)=0.44 e) Methyl 4-(4-chlorosulfonyl-3-pentafluorosulfanylphenoxy)-5-methanesulfonyl-2-methylbenzoate

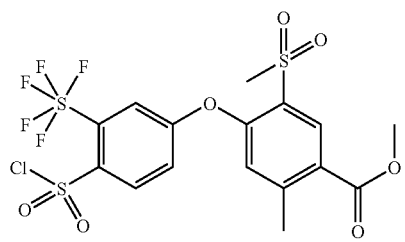

3.4 g of methyl 4-(4-amino-3-pentafluorosulfanylphenoxy)-5-methanesulfonyl-2-methyl-benzoate were dissolved in 30 ml of HOAc, and 30 g of ice and then 30 ml of a saturated aqueous HCl solution were added. A solution of 0.56 g of NaNO$_2$ in 5 ml of water was added dropwise to this solution at 0° C. over the course of 5 minutes. The mixture was stirred at 0° C. for 10 minutes. This solution was then added in portions to a suspension, cooled to 0° C., of 12.4 mg of CuCl and 125.6 mg of CuCl$_2$ (dihydrate) in 100 ml of an SO$_2$-saturated HOAc. The mixture was stirred at RT for 2 h and then diluted with 300 ml of water and extracted 3 times with 200 ml of EA each time. After drying over MgSO$_4$, the solvent was removed in vacuo. 3.5 g of a viscous oil were obtained and were reacted further without purification.

f) Sodium 4-(2-methanesulfonyl-4-methoxycarbonyl-5-methylphenoxy)-2-pentafluorosulfanylbenzenesulfinate

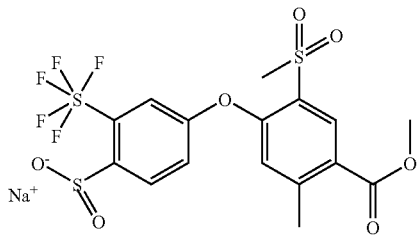

3.5 g of methyl 4-(4-chlorosulfonyl-3-pentafluorosulfanylphenoxy)-5-methanesulfonyl-2-methylbenzoate were added in portions to a solution of 8.10 g of Na$_2$SO$_3$ in 75 ml of water at 70° C., during which the pH was kept at about pH=10 with 10 molar aqueous NaOH solution. The mixture is then stirred at 70° C. for 45 minutes and, after being allowed to cool, the pH is adjusted to pH=2 with aqueous HCl solution. 3 extractions with 200 ml of EA each time were carried out. After drying over MgSO$_4$, the solvent was removed in vacuo. The residue was suspended in 100 ml of water and adjusted to pH=10 with a 2 molar aqueous NaOH solution, and the volatiles were removed in vacuo. Coevaporation was then carried out firstly twice with 100 ml of toluene each time and then with 100 ml of anhydrous DMF, and the residue (3.0 g) was reacted further without purification.

g) Methyl 5-methanesulfonyl-4-(4-methanesulfonyl-3-pentafluorosulfanylphenoxy)-2-methylbenzoate and methyl 5-methanesulfonyl-4-(4-methoxysulfinyl-3-pentafluorosulfanylphenoxy)-2-methylbenzoate

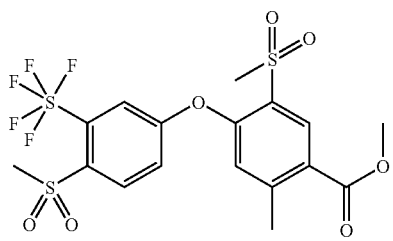

-continued

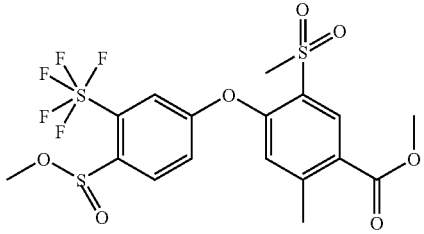

3.0 g of sodium 4-(2-methanesulfonyl-4-methoxycarbonyl-5-methylphenoxy)-2-pentafluorosulfanylbenzenesulfinate were dissolved in 100 ml of anhydrous DMF, 4.0 g of CH$_3$I were added, and the mixture was stirred at 45° C. for 9 h. The reaction mixture was then left to stand at RT for 2 days. The solvent was then removed in vacuo, and the residue was taken up in 100 ml of water and 100 ml of EA. 50 ml of a 5% aqueous NaHSO$_4$ solution were then added, and the phases were separated. This was followed by extraction 3 times with 100 ml of EA each time. After drying over MgSO$_4$, the solvent was removed in vacuo, and the residue was chromatographed on silica gel with MTB/DIP 1:1. 0.59 g of methyl 5-methanesulfonyl-4-(4-methanesulfonyl-3-pentafluorosulfanylphenoxy)-2-methylbenzoate and 0.49 g of methyl 5-methanesulfonyl-4-(4-methoxysulfinyl-3-pentafluorosulfanylphenoxy)-2-methyl-benzoate.

Rf (MTB/DIP 1:1)=0.13: methyl 5-methanesulfonyl-4-(4-methanesulfonyl-3-pentafluorosulfanylphenoxy)-2-methylbenzoate Rf (MTB/DIP 1:1)=0.32: methyl 5-methanesulfonyl-4-(4-methoxysulfinyl-3-pentafluorosulfanylphenoxy)-2-methylbenzoate h) N-[5-methanesulfonyl-4-(4-methanesulfonyl-3-pentafluorosulfanylphenoxy)-2-methylbenzoyl] guanidine

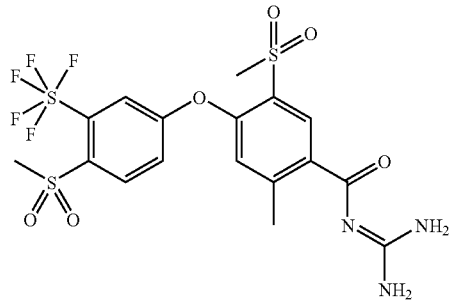

546 mg of guanidinium chloride and 535 mg of KOtBu were stirred in 20 ml of anhydrous DMF at RT for 30 minutes. Then 500 mg of methyl 5-methanesulfonyl-4-(4-methanesulfonyl-3-pentafluorosulfanylphenoxy)-2-methylbenzoate were added, and the mixture was left to stand at RT for 16 h. The reaction mixture was poured into 20 ml of water, adjusted to pH=8 with aqueous HCl solution and extracted 3 times with 50 ml of EA each time. The combined EA phases were then washed with 20 ml of a 5% aqueous NaHCO$_3$ solution and dried over MgSO$_4$, and the solvent was removed in vacuo. 420 mg of an amorphous solid were obtained.

| $R_f$ (EA/MeOH 10:1) = 0.29 | MS (ES$^+$) 551 |
|---|---| k) N-[5-methanesulfonyl-4-(4-methanesulfonyl-3-pentafluorosulfanylphenoxy)-2-methylbenzoyl]guanidine, hydrochloride

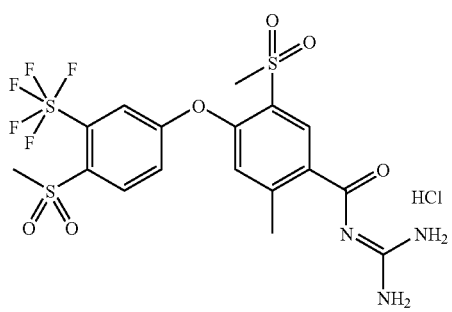

400 mg of N-[5-methanesulfonyl-4-(4-methanesulfonyl-3-pentafluorosulfanylphenoxy)-2-methylbenzoyl]guanidine were dissolved in dilute aqueous HCl solution and then the volatiles were removed in vacuo. The residue was recrystallized from water to result in 200 mg of a pale gray solid, mp 275° C.

Determination of NHE Inhibition

The inhibitory concentration $IC_{50}$ for NHE-1 inhibition was determined as follows:

$IC_{50}$ for NHE-1 inhibition were determined in a FLIPR assay by measurement of the recovery in $pH_i$ in transfected cell lines which express human NHE-1.

The assay was carried out in an FLIPR (fluorescent imaging plate reader) with black-walled 96-well microtiter plates with clear bases. The transfected cell lines expressing the various NHE subtypes (the parental cell line LAP-1 shows no endogenous NHE activity as a result of mutagenesis and subsequent selection) were seeded the preceding day at a density of ~25 000 cells/well.

The growth medium for the transfected cells (Iscove+10% fetal calf serum) additionally contained G418 as selection antibiotic in order to ensure the presence of the transfected sequences.

The actual assay started with the removal of the growth medium and addition of 100 µl of loading buffer per well (5 µM BCECF-AM [2',7'-bis(carboxyethyl)-5-(and -6-)carboxyfluorescein, acetoxymethyl ester] in 20 mM NH$_4$Cl, 115 mM choline chloride, 1 mM MgCl$_2$, 1 mM CaCl$_2$, 5 mM KCl, 20 mM HEPES, 5 mM glucose; pH 7.4 [adjusted with KOH]). The cells were then incubated at 37° C. for 20 minutes. This incubation led to loading of the cells with the fluorescent dye whose fluorescence intensity depends on pHi, and with NH$_4$Cl which makes the cells slightly alkaline. The nonfluorescent dye precursor BCECF-AM is, as ester, membrane-permeable. The actual dye BCECF is not membrane-permeable but is liberated inside cells by esterases.

After this incubation for 20 minutes, the loading buffer which contained NH$_4$Cl and free BCECF-AM was removed by washing three times in a cell washer (Tecan Columbus) with in each case 400 µl of washing buffer (133.8 mM choline chloride, 4.7 mM KCl, 1.25 mM MgCl$_2$, 1.25 mM CaCl$_2$, 0.97 mM K$_2$HPO$_4$, 0.23 mM KH$_2$PO$_4$, 5 mM HEPES, 5 mM glucose; pH 7.4 [adjusted with KOH]). The residual volume remaining in the wells was 90 µl (50-125 µl possible). This washing step removed the free BCECF-AM and resulted, as a consequence of the removal of the external NH$_4^+$ ions, in intracellular acidification (~pH$_i$ 6.3-6.4).

Since the equilibrium of intracellular NH$_4^+$ with NH$_3$ and H$^+$ was disturbed by the removal of the extracellular NH$_4^+$ and by the subsequent instantaneous passage of the NH$_3$ through the cell membrane, the washing process resulted in H$^+$ remaining inside the cells, which was the cause of the intracellular acidification. This may eventually lead to cell death if it persists long enough.

It was important at this point that the washing buffer was sodium-free (<1 mM) because extracellular sodium ions would lead to an instantaneous recovery of the pH$_i$ through the activity of the cloned NHE isoforms.

It was likewise important for all the buffers used (loading buffer, washing buffer, recovery buffer) not to contain any HCO$_3^-$ ions, because the presence of bicarbonate would lead to activation of interfering bicarbonate-dependent pH$_i$ regulatory systems present in the parental LAP-1 cell line.

The microtiter plates with the acidified cells were then (up to 20 minutes after the acidification) transferred to the FLIPR. In the FLIPR, the intracellular fluorescent dye was excited by light with a wavelength of 488 nm generated by an argon laser, and the measured parameters (laser power, illumination time and aperture of the CCD camera incorporated in the FLIPR) were chosen so that the average fluorescence signal per well was between 30 000 and 35 000 relative fluorescence units.

The actual measurement in the FLIPR started with a photograph being taken by the CCD camera every two seconds under software control. After ten seconds, the recovery of the intracellular pH was initiated by adding 90 µl of recovery buffer (133.8 mM NaCl, 4.7 mM KCl, 1.25 mM MgCl$_2$, 1.25 mM CaCl$_2$, 0.97 mM K$_2$HPO$_4$, 0.23 mM KH$_2$PO$_4$, 10 mM HEPES, 5 mM glucose; pH 7.4 [adjusted with NaOH]) by means of the 96-well pipettor incorporated in the FLIPR.

Positive control wells (100% NHE activity) were those to which pure recovery buffer was added, while negative controls (0% NHE activity) received washing buffer.

Recovery buffer with twice the concentration of test substance was added to all the other wells. Measurement in the FLIPR terminated after 60 measurements (two minutes).

The raw data are exported into the ActivityBase program. This program firstly calculates the NHE activities for each tested substance concentration and, from these, the IC$_{50}$ values for the substances. Since the progress of pH$_i$ recovery was not linear throughout the experiment, but fell at the end owing to decreasing NHE activity at higher pH$_i$ values, it was important to select for evaluation of the measurement the part in which the increase in fluorescence of the positive controls was linear.

| Example | NHE1 inhibition IC$_{50}$ [nM] |
|---|---|
| 1 | 33 |

The invention claimed is:
1. A pentafluorosulfanylbenzoylguanidine of the formula I:

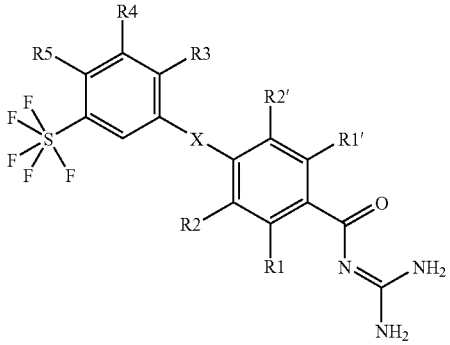

in which:
R1 and R1' independently of one another hydrogen, alkyl having 1, 2, 3 or 4 carbon atoms, alkoxy having 1, 2, 3 or 4 carbon atoms, F, Cl, Br, I, —CN, NR6R7, —O—$(CH_2)_b$—$(CF_2)_c$—$CF_3$ or —$(SO_d)_e$—$(CH_2)_f$—$(CF_2)_g$—$CF_3$;
R6 and R7 independently of one another hydrogen, alkyl having 1, 2, 3 or 4 carbon atoms or —$CH_2$—$CF_3$;
d is zero, 1 or 2;
b, c, e, f and g independently of one another zero or 1;
R2 and R2' are independently of one another hydrogen, F, Cl, Br, I, —CN, —$SO_2CH_3$, alkoxy having 1, 2, 3 or 4 carbon atoms, NR6R7, —O—$(CH_2)_b$—$(CF_2)_c$—$CF_3$, —$(SO_h)_k$—$(CH_2)_l$—$(CF_2)_m$—$CF_3$, alkyl having 1, 2, 3, 4, 5 or 6 carbon atoms, cycloalkyl having 3, 4, 5, 6, 7 or 8 carbon atoms, in which 1, 2, 3 or 4 hydrogen atoms may be replaced by fluorine atoms, —$(CH_2)_n$-phenyl which is unsubstituted or substituted by 1, 2 or 3 radicals selected from the group consisting of F, Cl, Br, I, —$O_o$—$(CH_2)_p$—$CF_3$, alkoxy having 1, 2, 3 or 4 carbon atoms, alkyl having 1, 2, 3 or 4 carbon atoms and —$SO_2CH_3$, or —$(CH_2)_q$-heteroaryl which is unsubstituted or substituted by 1, 2 or 3 radicals selected from the group consisting of F, Cl, Br, I, —$O_r$—$(CH_2)_s$—$CF_3$, alkoxy having 1, 2, 3 or 4 carbon atoms, alkyl having 1, 2, 3 or 4 carbon atoms and —$SO_2CH_3$;
R6 and R7 are independently of one another hydrogen, alkyl having 1, 2, 3 or 4 carbon atoms or —$CH_2$—$CF_3$;
b and c independently of one another zero or 1;
h is zero, 1 or 2;
k is zero or 1;
l is zero, 1, 2, 3, or 4;
m and o independently of one another are zero or 1;
p is zero, 1, 2 or 3;
n is zero, 1, 2, 3 or 4;
r is zero or 1;
s is zero, 1, 2 or 3;
q is zero, 1, 2, 3, or 4;
R3 is hydrogen, F, Cl, Br, I, —CN, —$SO_2CH_3$, alkyl having 1, 2, 3, 4, 5 or 6 carbon atoms, alkoxy having 1, 2, 3 or 4 carbon atoms or —$O_t$—$(CH_2)_u$—$CF_3$;
t is zero or 1;
u is zero, 1, 2 or 3;
R4 is hydrogen, F, Cl, Br, I, —CN, —$SO_2CH_3$, NR6R7, —$(SO_v)_w$—$(CH_2)_x$—$(CF_2)_y$—$CF_3$, —O—$(CH_2)_{aa}$—$(CF_2)_{bb}$—$CF_3$, alkyl having 1, 2, 3, 4, 5 or 6 carbon atoms, alkoxy having 1, 2, 3 or 4 carbon atoms or cycloalkyl having 3, 4, 5, 6, 7 or 8 carbon atoms, in which 1, 2, 3 or 4 hydrogen atoms may be replaced by fluorine atoms;
R6 and R7 are independently of one another hydrogen, alkyl having 1, 2, 3 or 4 carbon atoms or —$CH_2$—$CF_3$;
v is zero, 1 or 2;
x is zero, 1, 2, 3 or 4;
w, y, aa and bb independently of one another zero or 1;
or
R4 is —$(CH_2)_{cc}$-phenyl which is unsubstituted or substituted by 1, 2, or 3 radicals selected from the group consisting of F, Cl, Br, I, —$O_{dd}$—$(CH_2)_{ee}$—$CF_3$, alkoxy having 1, 2, 3 or 4 carbon atoms, alkyl having 1, 2, 3 or 4 carbon atoms and —$SO_2CH_3$;
dd is zero or 1;
ee is zero, 1, 2 or 3;
cc is zero, 1, 2, 3 or 4;
or
R4 is —$(CH_2)_{ff}$-heteroaryl which is unsubstituted or substituted by 1, 2 or 3 radicals selected from the group consisting of F, Cl, Br, I, —$O_{gg}$—$(CH_2)_{hh}$—$CF_3$, alkoxy having 1, 2, 3 or 4 carbon atoms, alkyl having 1, 2, 3 or 4 carbon atoms and —$SO_2CH_3$;
gg is zero or 1;
hh is zero, 1, 2 or 3;
ff is zero, 1, 2, 3 or 4;
R5 is F, Cl, Br, I, $CF_3$, —$SO_2CH_3$ or —$S(O)OCH_3$;
X a direct linkage, O, NR8, $S(O)_{kk}$;
R8 hydrogen, alkyl having 1, 2, 3 or 4 carbon atoms, —$(CH_2)_{mm}$—$CF_3$ or —$SO_2CH_3$ kk is zero, 1 or 2;
mm is zero, 1, 2 or 3;
where —O—$(CH_2)_b$—$(CF_2)_c$—$CF_3$ in the definitions of R1 and R1' and R2 and R2' can be selected independently of one another,
where NR6R7 in the definitions of R1 and R1', R2 and R2' and R4 can be selected independently of one another,
and the pharmaceutically acceptable salts thereof.

2. A compound of the formula I as claimed in claim 1, in which:
R1 and R1' are independently of one another hydrogen, alkyl having 1, 2, 3 or 4 carbon atoms, methoxy, ethoxy, F, Cl, NR6R7, —O—$CH_2$—$CF_3$ or —$(SO_d)_e$—$(CH_2)_f$—$CF_3$;
R6 and R7 are independently of one another hydrogen, alkyl having 1, 2, 3 or 4 carbon atoms or —$CH_2$—$CF_3$;
d is zero, 1 or 2;
e and f independently of one another zero or 1;
R2 and R2' are independently of one another hydrogen, F, Cl, —$SO_2CH_3$, —$(SO_h)_k$—$(CH_2)_l$—$CF_3$, alkyl having 1, 2, 3 or 4 carbon atoms, cycloalkyl having 3, 4, 5, 6 or 7 carbon atoms, in which 1, 2, 3 or 4 hydrogen atoms may be replaced by fluorine atoms, phenyl which is unsubstituted or substituted by 1-2 radicals selected from the group consisting of F, Cl, —$O_o$—$(CH_2)_p$—$CF_3$, methoxy, ethoxy, alkyl having 1, 2, 3 or 4 carbon atoms and —$SO_2CH_3$, or heteroaryl which is unsubstituted or substituted by 1-2 radicals selected from the group consisting of F, Cl, —$O_r$—$(CH_2)_s$—$CF_3$, methoxy, ethoxy, alkyl having 1, 2, 3 or 4 carbon atoms and —$SO_2CH_3$;
h is zero, 1 or 2;
k is zero or 1;
l is zero, 1, 2, 3, or 4;
o is zero or 1;
p is zero, 1, 2 or 3;

r is zero or 1;
s is zero, 1, 2 or 3;
R3 is hydrogen, F, Cl, —$SO_2CH_3$, alkyl having 1, 2, 3 or 4 carbon atoms, methoxy, ethoxy or —$O_t$—$(CH_2)_u$—$CF_3$,
t is zero or 1;
u is zero, 1, 2 or 3;
R4 is hydrogen, F, Cl, —$SO_2CH_3$, —$(SO_v)_w$—$(CH_2)_x$—$CF_3$, —O—$(CH_2)_{aa}$—$CF_3$, alkyl having 1, 2, 3 or 4 carbon atoms, methoxy, ethoxy or cycloalkyl having 3, 4, 5, 6 or 7 carbon atoms, in which 1, 2, 3 or 4 hydrogen atoms may be replaced by fluorine atoms;
v is zero, 1 or 2;
w, x, and aa
independently of one another zero or 1;
or
R4 is phenyl which is unsubstituted or substituted by 1-2 radicals selected from
the group consisting of F, Cl, —$O_{dd}$—$(CH_2)_{ee}$—$CF_3$, methoxy, ethoxy, alkyl having 1, 2, 3 or 4 carbon atoms and —$SO_2CH_3$;
dd and ee are independently of one another zero or 1;
or
R4 is heteroaryl which is unsubstituted or substituted by 1-2 radicals selected from the group consisting of F, Cl, —$O_{gg}$—$(CH_2)_{hh}$—$CF_3$, methoxy, ethoxy, alkyl having 1, 2, 3 or 4 carbon atoms and —$SO_2CH_3$;
gg and hh independently of one another zero or 1;
R5 is F, Cl, $CF_3$, —$SO_2CH_3$ or —$S(O)OCH_3$;
X is a direct linkage, O, NR8 or $S(O)_{kk}$;
R8 is hydrogen, alkyl having 1, 2, 3 or 4 carbon atoms, —$CH_2$—$CF_3$ or —$SO_2CH_3$;
kk is zero, 1 or 2;
and the pharmaceutically acceptable salts thereof.
3. A compound of the formula I as claimed in claim 1, in which the meanings are:
R1 and R1' are independently of one another hydrogen, alkyl having 1, 2, 3 or 4 carbon atoms, methoxy, ethoxy, F, Cl, NR6R7, —O—$CH_2$—$CF_3$ or —$(SO_d)_e$—$(CH_2)_f$—$CF_3$;
R6 and R7 independently of one another hydrogen, alkyl having 1, 2, 3 or 4 carbon atoms or —$CH_2$—$CF_3$;
d zero, 1 or 2;
e and f independently of one another zero or 1;
R2 and R2' independently of one another hydrogen, F, Cl, —$SO_2CH_3$, —$(SO_h)_k$—$(CH_2)_l$—$CF_3$, methyl, cycloalkyl having 3, 4, 5, 6 or 7 carbon atoms, in which 1, 2, 3 or 4 hydrogen atoms may be replaced by fluorine atoms, phenyl which is unsubstituted or substituted by a radical selected from the group consisting of F, Cl, —$O_o$—$(CH_2)_p$—$CF_3$, methoxy, ethoxy, alkyl having 1, 2, 3 or 4 carbon atoms and —$SO_2CH_3$, or heteroaryl which is unsubstituted or substituted by a radical selected from the group consisting of F, Cl, —$O_r$—$(CH_2)_s$—$CF_3$, methoxy, ethoxy, alkyl having 1, 2, 3 or 4 carbon atoms and —$SO_2CH_3$;
h is zero, 1 or 2;
k, l, o, p, r and s
independently of one another zero or 1;
R3 is hydrogen, F, Cl, —$SO_2CH_3$, methyl, methoxy, ethoxy or —$O_t$—$(CH_2)_u$—$CF_3$;
t and u independently of one another zero or 1;
R4 is hydrogen, F, Cl, —$SO_2CH_3$, —$(SO_v)_w$—$(CH_2)_x$—$CF_3$, —$O_z$—$(CH_2)_{aa}$—$CF_3$, methyl, methoxy, ethoxy or cycloalkyl having 3, 4, 5, 6 or 7 carbon atoms, in which 1, 2, 3 or 4 hydrogen atoms may be replaced by fluorine atoms;
v is zero, 1 or 2;
w, x, z and aa independently of one another zero or 1;
R5 is F, Cl or —$SO_2CH_3$;
X a direct linkage, O, NR8 or $S(O)_{kk}$;
R8 is hydrogen, methyl, ethyl, —$CH_2$—$CF_3$ or —$SO_2CH_3$;
kk is zero, 1 or 2;
and the pharmaceutically acceptable salts thereof.
4. A compound of the formula I as claimed in claim 1, in which:
R1 and R1' are independently of one another hydrogen, methyl, F, Cl, —$CF_3$ or —O—$CH_2$—$CF_3$;
R2 and R2' independently of one another hydrogen, F, Cl, —$SO_2CH_3$, —$SO_2$—$CF_3$, —$CF_3$ or methyl;
R3 is hydrogen, F, Cl or methyl;
R4 is hydrogen, F, Cl or methyl;
R5 is —$SO_2CH_3$;
X O;
and the pharmaceutically acceptable salts thereof.
5. A compound of the formula I as claimed in claim 1 selected from:
N-[5-methanesulfonyl-4-(4-methanesulfonyl-3-pentafluorosulfanylphenoxy)-2-methyl-benzoyl]guanidine or its pharmaceutically acceptable salts.
6. A process for preparing a compound of the formula I as claimed in claim 1, and/or the pharmaceutically acceptable salts thereof, which comprises reacting a compound of the formula VI:

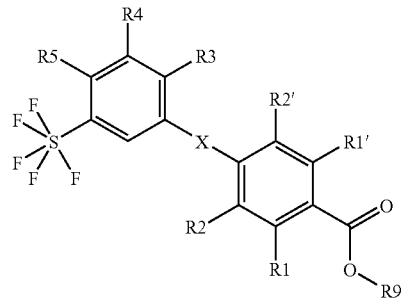

where R1, R1', R2, R2', R3, R4, R5 and X have the above-mentioned meanings, and R9 is hydrogen or alkyl having 1, 2, 3 or 4 carbon atoms with guanidine.
7. The compound of the formula I and/or the pharmaceutically acceptable salts thereof as claimed in claim 1 for use as medicament.
8. A pharmaceutical composition comprising an effective amount of a compound of the formula I and/or the pharmaceutically acceptable salts thereof as claimed in claim 1, together with pharmaceutically acceptable carriers and additives.
9. A pharmaceutical composition comprising an effective amount of a compound of the formula I and/or the pharmaceutically acceptable salts thereof as claimed in claim 1, together with pharmaceutically acceptable carriers and additives in combination with other pharmacological active ingredients or medicaments.

* * * * *